(12) United States Patent
Mikulka et al.

(10) Patent No.: US 7,794,410 B2
(45) Date of Patent: Sep. 14, 2010

(54) TISSUE SAMPLING DEVICE AND METHOD

(75) Inventors: Thomas Luke Mikulka, Cape Elizabeth, ME (US); Nevena Novkovic Djuranovic, South Portland, ME (US); Stanislaw Barski, Jr., Limerick, ME (US); Tracy Lynn Hessel Libby, North Yarmouth, ME (US)

(73) Assignee: Idexx Laboratories, Inc., Westbrook, ME (US)

( * ) Notice: Subject to any disclaimer, the term of this patent is extended or adjusted under 35 U.S.C. 154(b) by 725 days.

(21) Appl. No.: 11/012,395

(22) Filed: Dec. 15, 2004

(65) Prior Publication Data

US 2005/0131313 A1 Jun. 16, 2005

Related U.S. Application Data

(60) Provisional application No. 60/530,472, filed on Dec. 16, 2003, provisional application No. 60/547,599, filed on Feb. 25, 2004, provisional application No. 60/548,671, filed on Feb. 27, 2004, provisional application No. 60/548,749, filed on Feb. 27, 2004, provisional application No. 60/565,899, filed on Apr. 26, 2004.

(51) Int. Cl.
*A61B 10/02* (2006.01)
*A61B 10/00* (2006.01)
*A61B 17/32* (2006.01)

(52) U.S. Cl. .................. 600/567; 600/562; 600/564; 606/167; 606/184

(58) Field of Classification Search ............... 600/564, 600/565, 566, 567, 562; 606/167, 184
See application file for complete search history.

(56) References Cited

U.S. PATENT DOCUMENTS

| 241,864 A | 5/1881 | Huner |
| 1,191,831 A | 7/1916 | Royer et al. |
| 2,764,981 A | 10/1956 | Helmer et al. |
| 3,577,979 A | 5/1971 | Van der Gaast |
| 3,990,446 A | 11/1976 | Taylor |
| 4,116,247 A | 9/1978 | Zanasi |
| 4,142,517 A | 3/1979 | Stavropoulos et al. |
| 4,346,708 A | 8/1982 | LeVeen et al. |
| 4,549,612 A | 10/1985 | Cushing |
| 4,735,905 A | 4/1988 | Parker |
| 4,873,991 A * | 10/1989 | Skinner ................ 600/567 |

(Continued)

FOREIGN PATENT DOCUMENTS

DE 94 14 070 11/1994

(Continued)

*Primary Examiner*—Max Hindenburg
*Assistant Examiner*—Emily M Lloyd
(74) *Attorney, Agent, or Firm*—Carter, DeLuca, Farrell & Schmidt, LLP

(57) ABSTRACT

A device for obtaining a sample from inside a body includes a tubular body portion defining a chamber for receiving a sample of material therein; a plunger assembly operatively associated with the tubular body portion, the plunger assembly having a stopper slidably disposed within the chamber of the body portion; feedback elements provided on the tubular body and/or the plunger assembly for providing a user with audible and/or tactile indications regarding an amount of displacement of the plunger assembly relative to the body portion; and a cutting element is provided to facilitate sample removal.

21 Claims, 10 Drawing Sheets

U.S. PATENT DOCUMENTS

| | | |
|---|---|---|
| 4,919,146 A | 4/1990 | Rhinehart et al. |
| 4,956,297 A | 9/1990 | Hood et al. |
| 5,133,360 A | 7/1992 | Spears |
| 5,304,124 A | 4/1994 | Essig |
| 5,324,300 A | 6/1994 | Elias |
| 5,357,974 A | 10/1994 | Baldridge |
| 5,375,608 A | 12/1994 | Tiefenbrun et al. |
| 5,380,492 A | 1/1995 | Seymour |
| 5,423,809 A | 6/1995 | Klicek |
| 5,462,062 A * | 10/1995 | Rubinstein et al. ........ 600/567 |
| 5,582,595 A | 12/1996 | Haber et al. |
| 5,786,227 A | 7/1998 | Charlton |
| 5,786,228 A | 7/1998 | Charlton |
| 5,810,806 A | 9/1998 | Ritchart et al. |
| 5,823,971 A | 10/1998 | Robinson et al. |
| 5,833,628 A * | 11/1998 | Yuan et al. .................. 600/567 |
| 5,925,834 A | 7/1999 | Sgourakes |
| 5,961,458 A * | 10/1999 | Carroll ....................... 600/562 |
| 5,981,293 A | 11/1999 | Charlton |
| 6,168,576 B1 | 1/2001 | Reynolds |
| 6,176,326 B1 | 1/2001 | David et al. |
| 6,299,842 B1 | 10/2001 | Kozak et al. |
| 6,395,011 B1 * | 5/2002 | Johanson et al. ............ 600/567 |
| 6,579,269 B1 | 6/2003 | Kleyman |
| 6,792,305 B2 * | 9/2004 | Rastorgoueff et al. ....... 600/547 |
| 6,972,006 B2 * | 12/2005 | Ferguson .................... 604/208 |
| 2002/0164272 A1 | 11/2002 | Harris |
| 2002/0182718 A1 | 12/2002 | Malmquist |
| 2003/0225358 A1 | 12/2003 | Berman et al. |
| 2004/0054332 A1 | 3/2004 | Ferguson |

FOREIGN PATENT DOCUMENTS

| | | |
|---|---|---|
| FR | 2585233 | 1/1987 |
| WO | WO97/36160 | 10/1997 |
| WO | WO 99/23950 | 5/1999 |

* cited by examiner

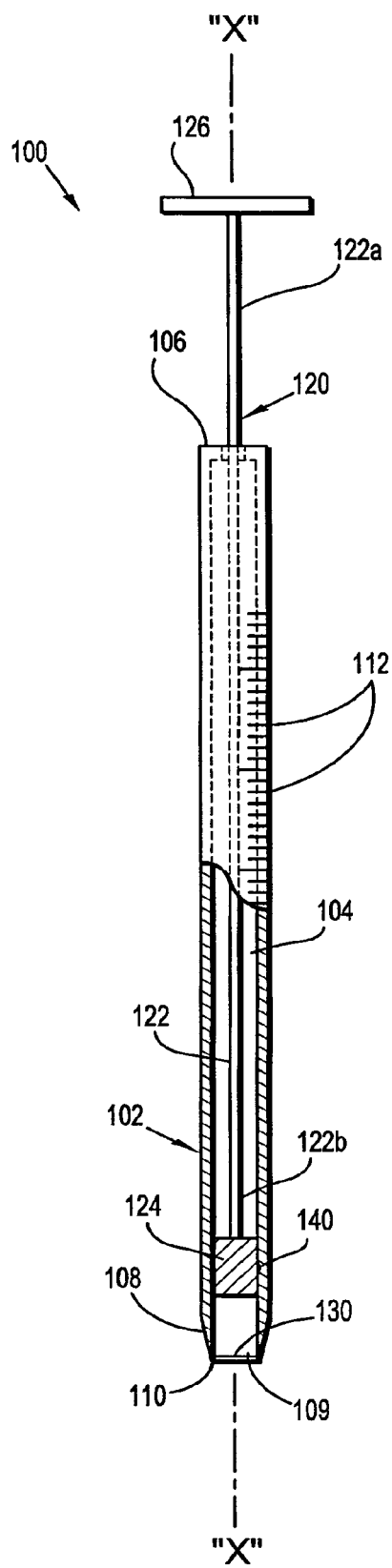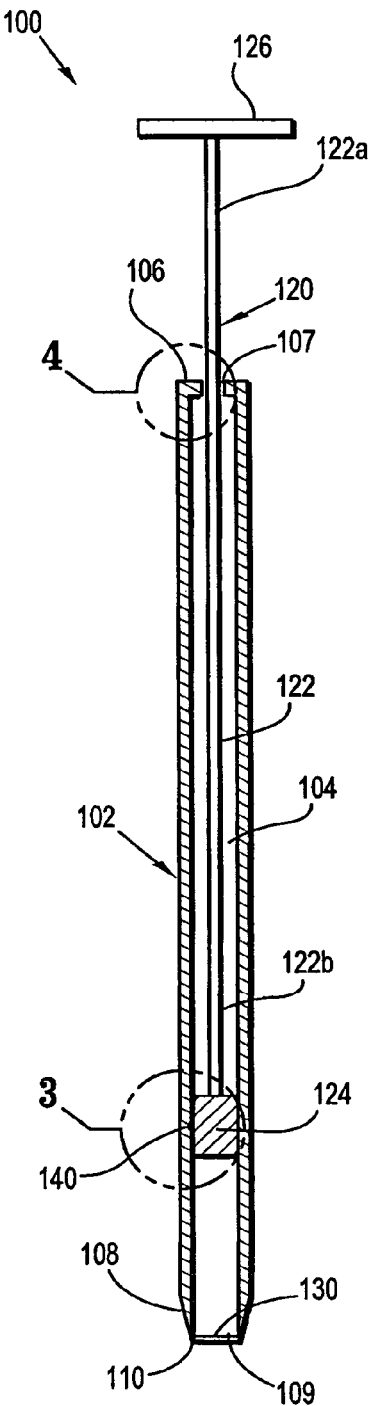
FIG. 1    FIG. 2

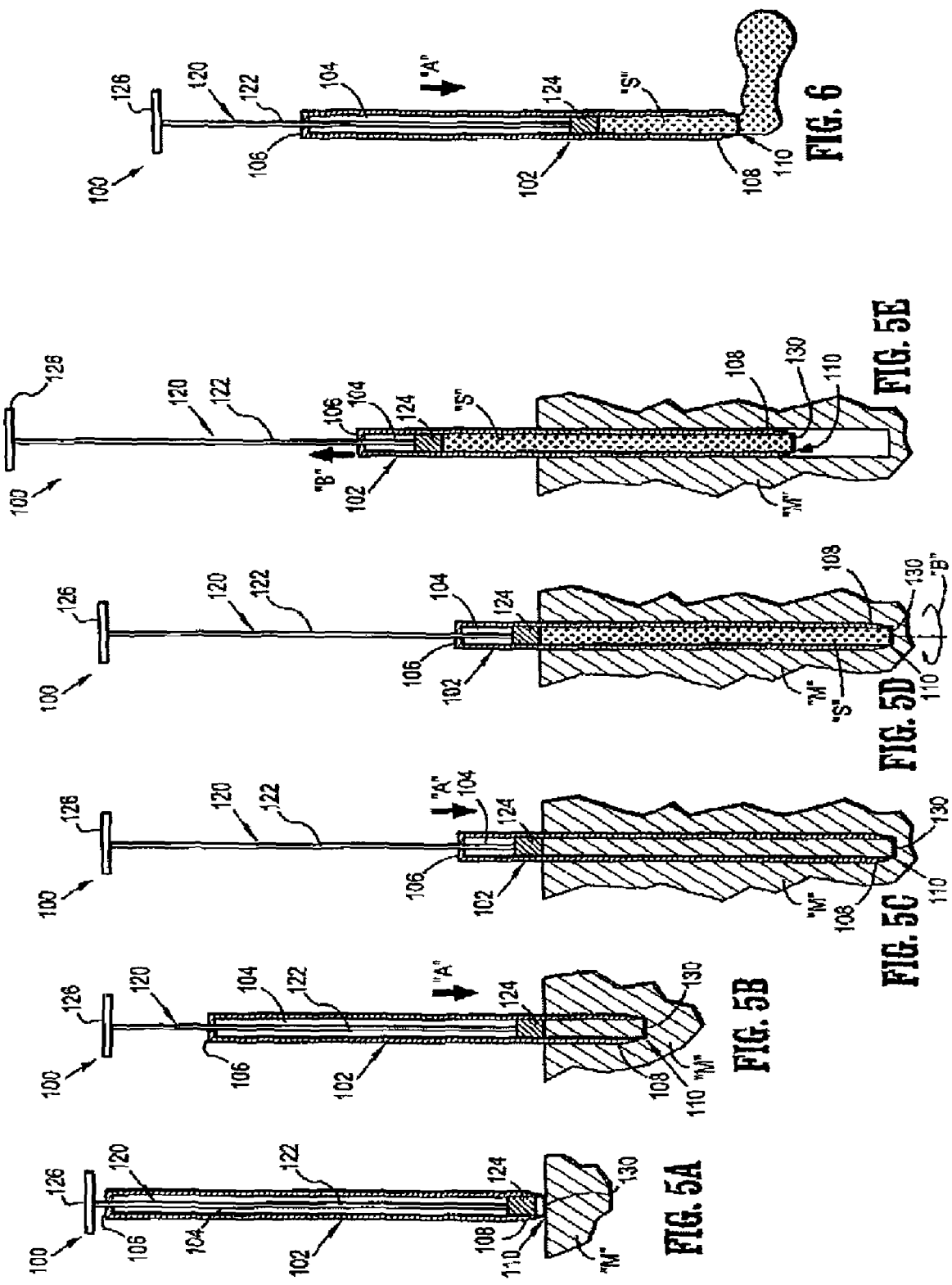

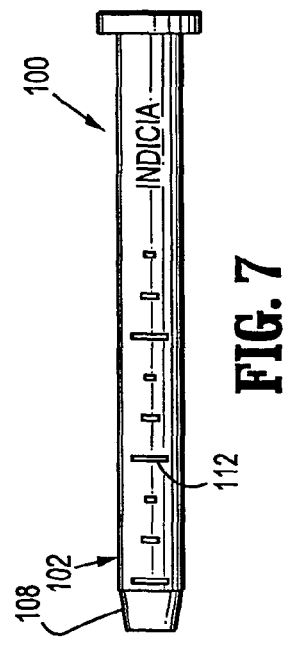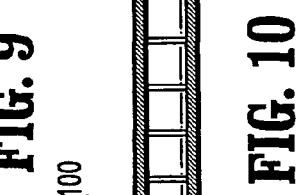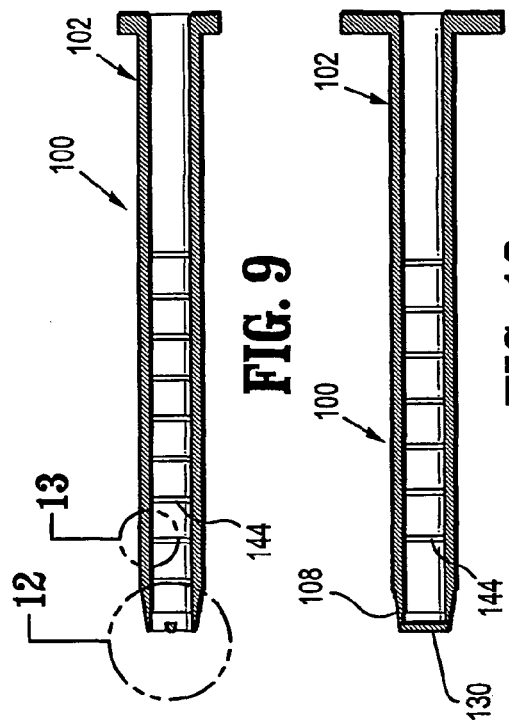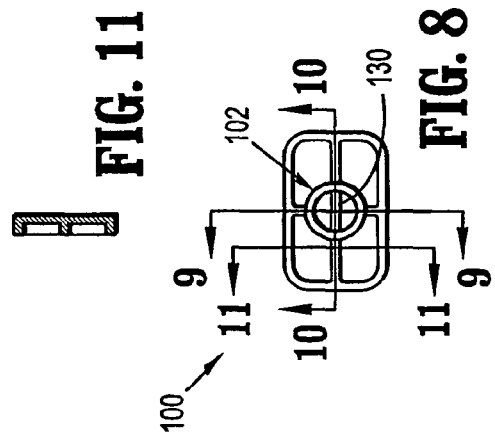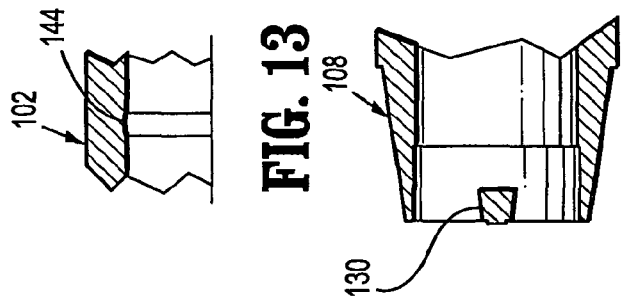

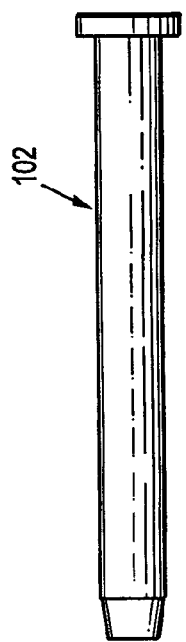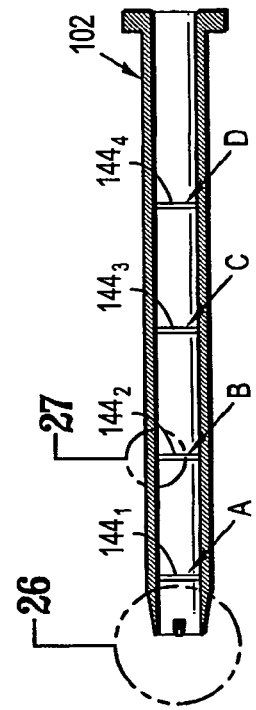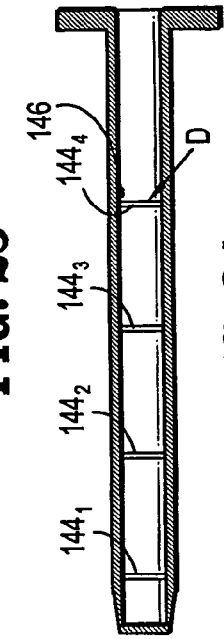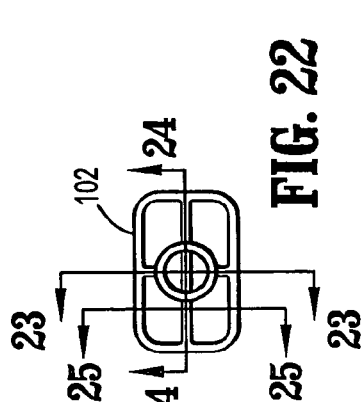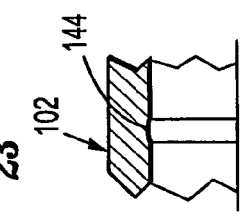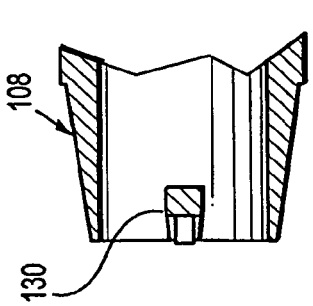
FIG. 21
FIG. 23
FIG. 24
FIG. 25
FIG. 22
FIG. 27
FIG. 26

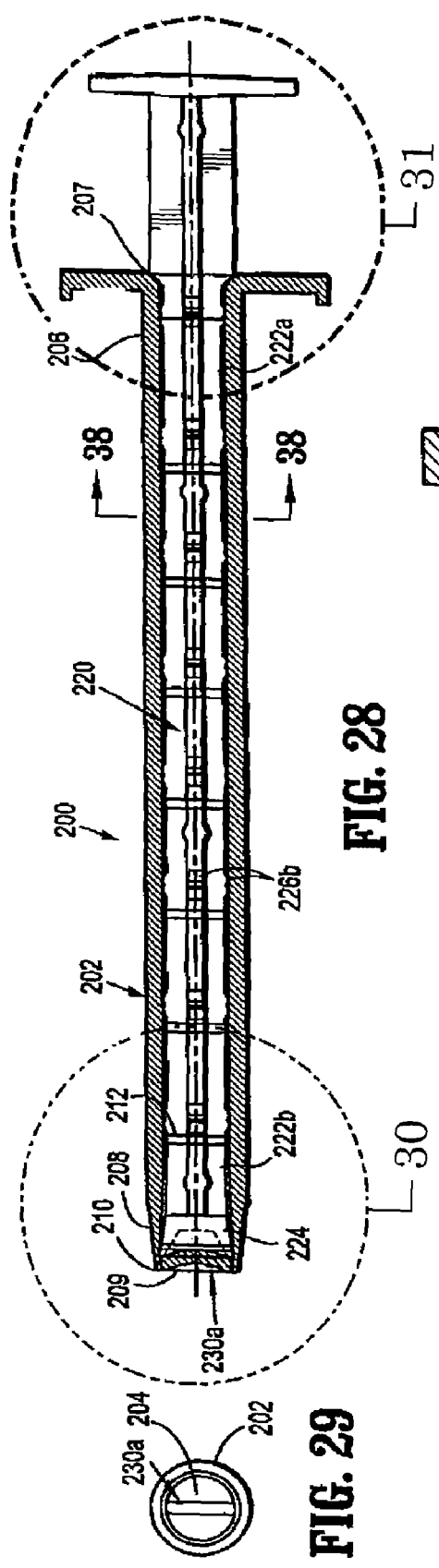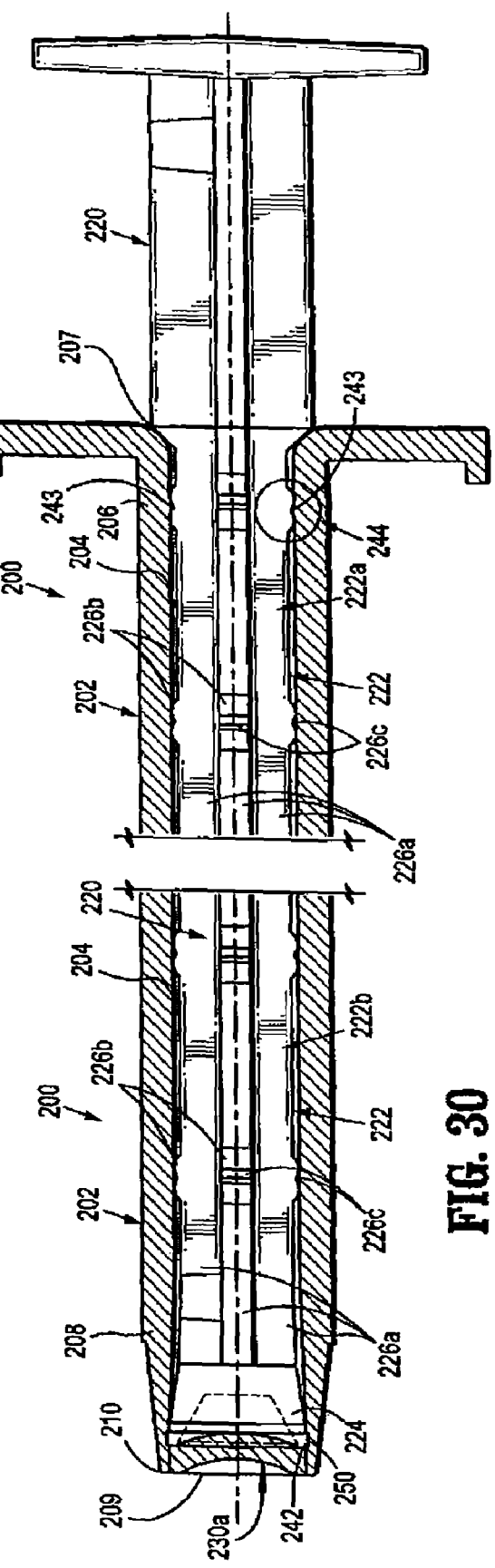

TISSUE SAMPLING DEVICE AND METHOD

CROSS-REFERENCE TO RELATED APPLICATIONS

The present application claims the benefit of and priority to U.S. Provisional Application No. 60/530,472, filed on Dec. 16, 2003; U.S. Provisional Application No. 60/547,599, filed on Feb. 25, 2004; U.S. Provisional Application No. 60/548,671, filed on Feb. 27, 2004; U.S. Provisional Application No. 60/548,749, filed on Feb. 27, 2004; and U.S. Provisional Application No. 60/565,899, filed on Apr. 26, 2004, the entire contents of each of which being incorporated herein by reference.

BACKGROUND

1. Technical Field

The present disclosure is directed to tissue sampling devices and, more particularly, to tissue sampling devices including sensory feedback elements and methods of using the same.

2. Discussion of Related Art

In general, sampling devices, e.g., pipettes, syringes, etc., consist of a cylindrical barrel having a distal end adapted to permit passage of biological materials therethrough and a proximal end adapted to receive a stopper and plunger rod assembly. The stopper functions to provide a fluid tight seal between itself and the barrel so that movement of the stopper along the barrel will cause the biological material to be drawn into or forced out of the barrel through the distal end. The stopper is moved along the barrel by applying axial force to the plunger rod which is connected to the stopper. The plunger rod is sufficiently long to be accessible outside of the barrel. Typically, indicia, such as volume measuring indicia, are provided along the length of the barrel to indicate to the user the volume of the biological material contained within the barrel.

The material drawn into or forced out of the sampling device can consist of biological fluids, e.g., blood, plasma, serum, urine, cerebrospinal fluid, etc., or solids, e.g., organs, tissue fragments, etc., which are not distributed in a systematically homogeneous manner in the sampling device as compared to biological fluid. In instances where biological solids are involved, the collection and sampling process becomes more complex and the devices often have to be adapted to each particular case according to the greater of lesser fluidity or viscosity of the biological solids.

Analysis of biological solids is currently performed in the diagnosis of a number of diseases, such as, for example, the diagnosis of transmissible spongiform encephalopathies (TSE), which are degenerative neurological diseases, e.g., scrapie in sheep, "mad cow disease", also called bovine spongiform encephalopathy (hereafter "BSE"), in cattle, Creutzfeldt-Jakob disease (CJD) and kuru in humans, and related transmissible spongiform encephalopathies.

In the case of BSE, diagnosis currently requires a biological sample to be collected from the brain matter, especially from the animal's brain stem and more particularly from the sensory and motor nuclei of the vagus nerve, which constitute the zone of preferential accumulation of PrPres (abnormal form of a protein called "prion protein"), the diagnostic marker of BSE. The sample collected is then subjected to various treatments for extraction of PrPres which is then analyzed by immunoassay. In view of its plastic properties and its viscosity, bovine brain matter is not easy to sample in a simple, rapid, reproducible, quantifiable and safe manner.

For mass screenings of bovine carcasses, it is essential that the tests are affected in the simplest and quickest manner possible after slaughter and as reproducibly, quantifiably and safely as possible, i.e. with the best possible sensitivity and without external contamination.

There is, therefore, a continuing need for devices for collecting a soft biological sample, particularly brain matter, which is simple and/or quick to use, is economic, has a reproducible performance and is quantifiable, effective and safe from any external contamination. There is also a need for methods of carrying out this type of sampling.

"Soft biological sample" is to be understood as meaning a sample of a biological material whose consistency is such that it can be cut effortlessly with a tool such as a scalpel, e.g., brain matter. "Brain matter" is to be understood as meaning any portion of the mass constituting the central nervous system, and particularly, but not exclusively, the anatomical part conventionally called the "brain stem", especially that which is centered on the sensory and motor nuclei of the vagus nerve, whether said matter be in the natural state or whether it has been treated, e.g. obtained in the form of a pasty ground material.

SUMMARY

The present disclosure provides for devices for obtaining a sample from inside a body. According to one embodiment, the device includes a tubular body portion defining a chamber for receiving a sample of material therein; a plunger assembly operatively associated with the tubular body portion, the plunger assembly having a stopper slidably disposed within the chamber of the body portion; and feedback elements provided on the tubular body and/or the plunger assembly for providing a user of the sampling device with audible and/or tactile indications regarding an amount of displacement of the plunger assembly relative to the body portion. The stopper is adapted for fluid tight engagement with the body portion.

According to one aspect of the present disclosure the feedback elements may include a groove or a projection formed along an inner surface of the chamber of the tubular body portion. Preferably, the groove or projection is annular. It is envisioned that the annular groove corresponds with a metrical marking provided on the tubular body portion.

According to another aspect of the present disclosure, the tubular body portion may include a series of metrical markings formed along the length thereof, and a feedback element is provided in association with each metrical marking.

Desirably, the metrical markings are provided at least at 100 μL intervals from one another. It is envisioned that the rod of the plunger assembly may have a cruciform transverse cross-sectional profile.

It is envisioned that the distal end of the tubular body portion may have a frusto-conical shape over at least one of its outer and inner peripheries. The tubular body portion may define a distal cutting edge.

According to another aspect of the present disclosure, the plunger assembly includes a rod operatively connected to the stopper and extending from the proximal end of the body portion. The feedback elements may include a series of grooves or a series of projections formed along the length of the rod and either a groove or a projection provided at the proximal end of the tubular body for inter-engaging the grooves or projections provided on the rod.

According to an embodiment, the rod of the plunger assembly has a cruciform transverse cross-sectional profile. Desirably, each projection formed along the length of the rod includes a depression formed therein for selectively inter-engaging an annular rib extending from an inner surface of the body portion proximate a proximal end thereof. Desirably, the feedback elements include an annular rib extending from an inner surface of the body portion proximate a proximal end thereof.

Preferably, the device further includes at least one cutting element associated with the distal end of the tubular body portion. The cutting element may extend diametrically across the distal end. Alternatively, the cutting element can be angled and/or take the form of multiple elements that are either joined or extend partially across the distal end of the tubular body portion. In particular, the cutting element can include three arms extending radially inward from the inner surface of the body portion. The three arms can have free ends or be joined to one another at the longitudinal central axis of the body portion.

In another embodiment, the cutting element can be a pair of opposed arms extending radially inward from the inner surface of the body portion, and a third arm extending radially inward from the inner surface of the body portion. Desirably, the pair of arms extend toward the central longitudinal axis of the body portion. The third arm extends beyond the central longitudinal axis of the body portion. The third arm is disposed at a substantially equi-distant location between the pair of opposed arms. Preferably each arm includes an unsupported free end.

In yet another embodiment, the cutting element includes a plurality of arms extending radially inward from an inner surface of the body portion. Each arm desirably includes an unsupported free end. Preferably, the free ends of each of the arms do not extend across the central longitudinal axis of the body portion.

In still another embodiment, the cutting element includes at least a pair of arms extending inward from an inner surface of the body portion, wherein each arm includes a free end. Desirably, the pair of arms of the cutting element are parallel to, and spaced apart from one another. The pair of arms of the cutting element may extend in opposite directions to one another. Alternatively, the pair of arms of the cutting element may extend in the same direction as one another. Still further, the pair of arms may be orthogonal to one another.

According to another aspect of the present disclosure, a method of collecting a sample of material from a body is provided. The method includes the step of providing a device for obtaining the sample of material. The device includes a tubular body portion having an open distal end and defining a chamber for receiving the sample of material therein; a plunger assembly operatively associated with the tubular body portion and having a stopper slidably disposed within the chamber of the body portion, the stopper being adapted for fluid tight engagement with the body portion; feedback elements provided on the tubular body and/or the plunger assembly for providing a user of the sampling device with audible and/or tactile indications regarding an amount of displacement of the plunger assembly relative to the body portion; and a cutting element extending across an open distal end of the body portion.

The method further includes the steps of placing the open distal end of the device against the material from which the sample is to be taken; driving the body portion into the material an amount sufficient for a sample of the material to enter the chamber of the body portion; rotating the body portion about a longitudinal axis thereof an amount sufficient for the cutting element to sever the sample of material from the remainder of the material; and withdrawing the device from the material.

It is contemplated that the stopper of the plunger assembly is positioned proximate the distal end of the body portion when the device is driven into the material. Accordingly, as the body portion is driven into the material the stopper is displaced in an axially proximal direction relative to the body portion.

The feedback elements may include a series of annular grooves formed along the length of the chamber; and a projection extending radially outward from the stopper of the plunger assembly. Accordingly, as the stopper is displaced in a proximal direction, the projection of the stopper inter-engages with the annular grooves formed in the chamber.

The annular grooves are preferably provided at intervals which correspond to 100 μL of volume of the chamber of the body portion. The body portion may include a metrical marking for each annular groove.

In operation, as the body portion is driven into the material, the feedback elements provide the user with audible and/or tactile indications as to the volume of material collected into the chamber of the body portion.

The method further includes the step of driving the plunger assembly in a distal direction relative to the body portion to expel the sample therefrom. The feedback elements provide the user with audible and/or tactile indications as to the quantity of sample expelled from the chamber of the body portion.

Other objects and features of the present disclosure will become apparent from consideration of the following description taken in conjunction with the accompanying drawings.

BRIEF DESCRIPTION OF THE DRAWINGS

By way of example only, preferred embodiments of the disclosure will be described with reference to the accompanying drawings, in which:

FIG. 1 is a side elevational view, partially broken away, of a sampling device in accordance with an embodiment of the present disclosure;

FIG. 2 is a cross-sectional side elevational view of the sampling device of FIG. 1;

FIGS. 5A to 5E illustrate an exemplary method of using the sampling device of FIGS. 1 to 4 for the collection of a biological sample;

FIG. 6 illustrates a method of extruding the biological sample from the sampling device of FIGS. 1 to 4, in accordance with an embodiment of the present disclosure;

FIG. 7 is a side elevational view of the body portion of the sampling device of FIGS. 1 to 4;

FIG. 8 is an front elevational view of the body portion of FIG. 7;

FIG. 9 is a longitudinal cross-sectional view of the body portion of FIG. 7, as taken through 9-9 of FIG. 8;

FIG. 10 is a longitudinal cross-sectional view of the body portion of FIG. 7, as taken through 10-10 of FIG. 8;

FIG. 11 is a cross-sectional view of the body portion of FIG. 7, as taken through 11-11 of FIG. 8;

FIG. 12 is an enlarged view of the body portion of the area indicated 12 of FIG. 9;

FIG. 13 is an enlarged view of the body portion of the area indicated 13 of FIG. 9;

FIG. 21 is a side elevational view of the body portion of a sampling device according to another embodiment of the present disclosure;

FIG. 22 is an front elevational view of the body portion of FIG. 21;

FIG. 23 is a longitudinal cross-sectional view of the body portion of FIG. 21, as taken through 23-23 of FIG. 22;

FIG. 24 is a longitudinal cross-sectional view of the body portion of FIG. 21, as taken through 24-24 of FIG. 22;

FIG. 25 is a cross-sectional view of the body portion of FIG. 21, as taken through 25-25 of FIG. 22;

FIG. 26 is an enlarged view of the body portion of the area indicated 26 of FIG. 23;

FIG. 27 is an enlarged view of the body portion of the area indicated 27 of FIG. 23;

FIG. 28 is a longitudinal cross-sectional view of a sampling device in accordance with yet another embodiment of the present disclosure;

FIG. 29 is a distal end view of the sampling device of FIG. 28;

FIG. 30 is an enlarged view of the area indicated as 30 of the sampling device of FIG. 28;

FIG. 31 is an enlarged view of the area indicated as 31 of the sampling device of FIG. 28;

DETAILED DESCRIPTION OF PREFERRED EMBODIMENTS

Figure 3:
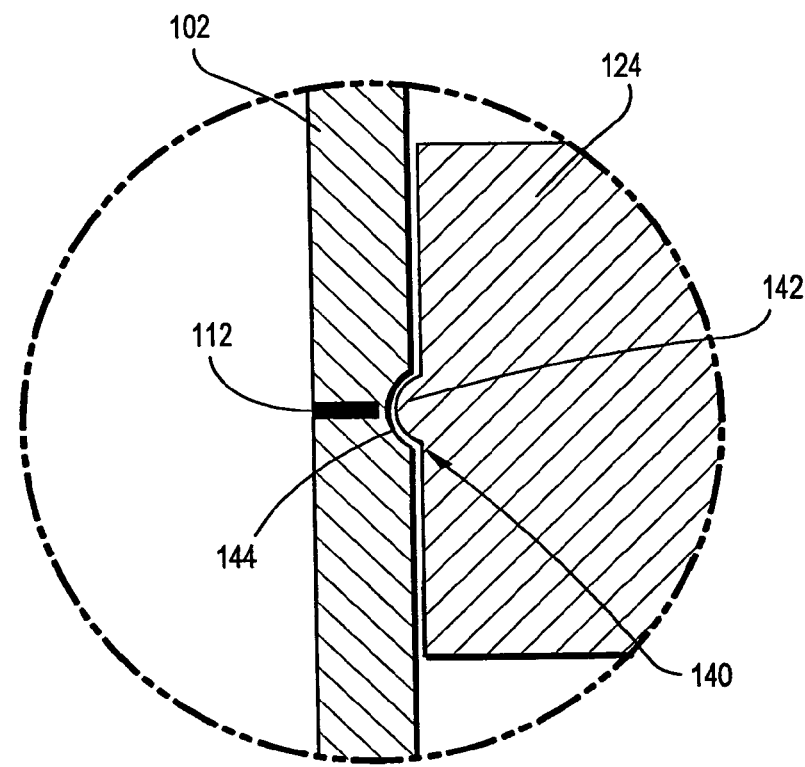
FIG. 3 is an enlarged side view of the area indicated as 3 of FIG. 2.

The present disclosure now will be described more fully hereinafter with reference to the accompanying drawings, in which preferred embodiments of the disclosure are shown. Referring to FIGS. 1-4, embodiments of sampling devices, in accordance with the present disclosure, are generally designated as 100. Although the presently disclosed sampling devices 100 will be described and illustrated hereinafter in connection with specific embodiments and uses, such as, for example, use in the medical field, it will be readily appreciated and understood by one skilled in the art that the presently disclosed sampling device 100 may be adapted for usage in other applications and fields of use as well.

In the drawings and in the description which follows, the term "proximal", as is traditional, will refer to the end of the device which is closest to the operator while the term "distal" will refer to the end of the device which is furthest away from the operator.

As seen in FIGS. 1-4, sampling device 100 includes a hollow cylindrical or tubular body portion 102 defining a chamber 104 therein and having a longitudinal axis "X". Preferably, body portion 102 is fabricated from a clear or transparent material such as a polypropylene and the like. Body portion 102 includes a proximal end 106 having an opening 107 and a distal end 108 having an opening 109. Distal end 108 is adapted to form a slicing edge 110 by gradually decreasing, in a distal direction, the thickness of the wall of body portion 102. As a result, distal end 108 can have a generally frusto-conical shape over its outer periphery, over its inner periphery or over both its outer and inner periphery. Alternatively, body portion 102 can have a blunt end. Chamber 104 of body portion 102 preferably has a volume which is equal to at least 300 μL.

Body portion 102 is provided with volume measuring indicia in the form of metrical markings 112, along substantially the entire length thereof, for use in determining the volume of material within chamber 104 of sampling device 100 and, in turn, the volume of material to be expunged from chamber 104 of sampling device 100. Indicia or markings 112 can be etched into body portion 102, printed on the outer or inner surface of body portion 102, or otherwise provided on the outer or inner surface of body portion 102. It is within the purview of the present disclosure to include some or all of these various means for providing volume measuring indicia on body portion 102. Indicia or markings 112 are preferably provided, at least at, 100 μL intervals from one another. In other words, each marking 112 marks-off 100 μL of volume of chamber 104 of body portion 102. While indicia or markings 112 are preferably provided at 100 μL from one another, it is envisioned and within the scope of the present disclosure for indicia or markings 112 to be spaced at any desired and/or operatively beneficial interval from one another.

Sampling device 100 further includes a plunger assembly 120 slidably positionable within chamber 104 of body portion 102. Plunger assembly 120 includes a movable piston rod 122 including a proximal end portion 122a extending from opening 107 of proximal end 106 of body portion 102 and a distal end portion 122b extending into chamber 104 of body portion 102. Piston rod 122 may be made of suitable material such as, for example, high density polyethylene (HDPE). Plunger assembly 120 further includes a stopper 124 operatively connected to distal end portion 122b of piston rod 122. Stopper 124 is slidably positioned within body portion 102, in fluid tight engagement therewith, and is capable of moving material from chamber 104, through opening 109 of distal end 108 of body portion 102, upon its distal axial movement relative to opening 109. Moreover, stopper 124 is capable of drawing material into chamber 104, through opening 109 of distal end 108 of body portion 102, upon placement of distal end 108 into fluid material and upon proximal axial movement of stopper 124 relative to opening 109 of distal end 108 of body portion 102. It is envisioned that stopper 124 may be fabricated from rubber or the like.

A cutting element 130, such as a cutting wire or integrally molded part, can be provided across distal end 108 of body portion 102. Preferably, cutting element 130 can extend diametrically across distal end 108 of body portion 102 (i.e. straight across and attached at each end). Cutting element 130 can be of circular, triangular or other cross-sectional profile. In general, any cross-sectional profile which is capable of giving element 130 a cutting effect when it is displaced relative to a sample of soft biological material is suitable.

Figure 19:
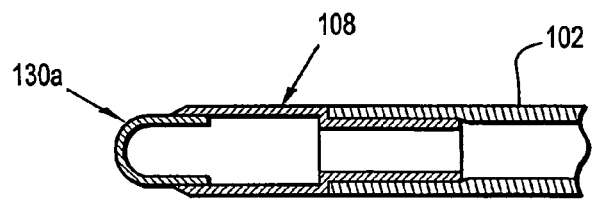
FIG. 19 is an enlarged partial longitudinal cross-section view of a distally extending arcuate cutting element in accordance with an embodiment of the present disclosure, positioned at the distal end of the body portion.

As seen in FIG. 19, a cutting element may take the form of an arcuate, a "U-shaped", or a "C-shaped" cutting element 130a which extends distally beyond distal end 108 of body portion 102. An example of such an arcuate cutting element is disclosed in WO 99/23950, the entire contents of which is incorporated herein by reference.

Figure 19A:
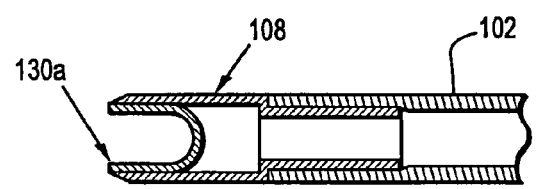
FIG. 19A is an enlarged partial longitudinal cross-section view of a proximally extending arcuate cutting element in accordance with an embodiment of the present disclosure, positioned at the distal end of the body portion.

Alternatively, as shown in FIG. 19A, arcuate cutting element 130a may extend proximally into body portion 102. In this configuration, there is the added advantage that the user may wipe distal end 108 clean without interfering with arcuate cutting element 130a. Other cutting element configurations are disclosed, supra.

Construction of arcuate cutting element 130a may be achieved by molding the entire arcuate cutting element as one unitary member or separately molding the multiple elements making up the arcuate cutting element and attaching the multiple elements to distal end 108 of body portion 102.

In one embodiment, sampling device 100 is provided with one or more sensory feedback elements 140, e.g., audible, tactile, etc., which provide the user with sensory indications as to the position of plunger assembly 120, in particular stopper 124, relative to body portion 102. Sensory feedback elements 140 can be provided, for example, at 100 µL, 200 µL or 300 µL increments along the length of body portion 102, preferably at 500 µL. For brain samples suspected of containing prion proteins, current tests typically require approximately 300 µL+/−10% to be dispensed from the device.

As seen in FIG. 3, feedback elements 140 include a nub or projection 142, preferably an annular nub or projection, extending radially outward from the surface of stopper 124 and an annular groove 144 formed in the inner surface of body portion 102. Preferably, projection 142 and annular grooves 144 have complementary cross-sectional profiles (e.g., rounded, pointed, squared and the like). In this manner, as stopper 124 is displaced through body portion 102, projection 142 engages and disengages grooves 144. The engagement and disengagement of projection 142 with grooves 144 creates at least one of an audile sound (e.g., a click) and a vibration or other tactile effect due to the temporary interruption of the smooth passage of stopper 124 through body portion 102 and along the inner surface of chamber 104.

Preferably, grooves (or protrusions) 144 are positioned along the length of body portion 102 such that stopper 124 and/or projections 142 engage grooves 144 at 300 µL intervals and/or at 150 µL. Accordingly, as the user displaces plunger assembly 120 in a distal or proximal direction, feedback elements 140 enable the user to readily ascertain the quantity of material drawn into chamber 104 or expunged from chamber 104 without having to make a visual observation and/or confirmation regarding the same.

Advantageously, during use, if distal end 108 of body portion 102 is imbedded or buried in material, wherein the optional visual volume measuring indicia or markings 112 are obscured or otherwise not visible, feedback elements 140 enable the user to draw in or expunge the desired and/or necessary amount of material into/from chamber 104 of body portion 102. Previously, tissue sampling devices requiring visual observation of the quantity of their contents, were generally filled completely to ensure enough material was drawn into the chamber and/or needed to be reintroduced into the site to draw in additional material if not enough material was drawn into the chamber during the first insertion.

While feedback elements 140 can include an annular projection 142 extending from stopper 124 and annular grooves 144 formed in the inner surface of body portion 102, it is envisioned that feedback elements 140 can include a series of projections, preferably bumps or annular projections, extending radially inward from the inner surface of body portion 102 at predetermined locations (not shown). In such an embodiment, stopper 124 can have an annular groove formed on the outer surface thereof or merely interact with the projections as a surface (such as the proximal or distal end portion) of the stopper passes by the projection(s).

Alternatively, as seen in FIGS. 7-13 and 21-27, and in particular in FIGS. 9, 10, 13, 23, 24 and 27, it is further envisioned that, feedback elements 140 can include a series of grooves 144 formed along the inner surface of body portion 102. In this manner, as stopper 124 of plunger assembly 120 passes over grooves 144, stopper 124 inter-engages grooves 144 and creates an effect which can be tactilely sensed. In particular, as previously stated, the inner surface of body portion 102 preferably includes one or more grooves 144 or protrusions (not shown) formed therein that interact with stopper 124 of plunger assembly 120 to provide tactile feedback to the user as stopper 124 traverses body portion 102. As seen in FIG. 24, four grooves $144_{1-4}$ are formed at predetermined locations along the inner surface of body portion 102. Fewer or more grooves 144 may be provided as desired.

Grooves 144 may be formed to extend at least partially, preferably completely, around the entire inner circumference of body portion 102 at the predetermined locations. By varying the depth of grooves 144 or the height of the protrusions and the degree to which such groove 144 or protrusion is present (i.e., partially or completely around the inner circumference of body portion 102), the degree of resistance to movement experienced by stopper 124 of plunger assembly 120 may be varied. Grooves 144 and protrusions may be formed adjacent one another to achieve the desired tactile resistance (e.g., as seen in FIG. 24, a stopping element 146, extending from the inner surface of body portion 102, may be formed adjacent proximal-most groove $144_4$).

It has been determined that there may be an advantage to having the proximal-most tactile indicator or feedback element be of greater resistance than the other tactile indicators or feedback elements. This would allow the user to withdraw piston assembly 120 to a point corresponding to the proximal-most position and, through tactile feedback, understand that plunger assembly 120 is at this position due to resistance that is greater than other tactile indicator locations. Determination of the proximal-most position of plunger assembly 120 is useful so that the user knows the starting point of plunger assembly 120 (without having to look at the device) before plunger assembly 120 is moved in the distal direction (i.e., to expel tissue and/or fluids contained in body portion 102). Tactile indication of a proximal location of plunger assembly 120 also indicates that further proximal movement of plunger assembly 120 may cause plunger assembly 120 to be completely withdrawn from body portion 102.

Figure 4:
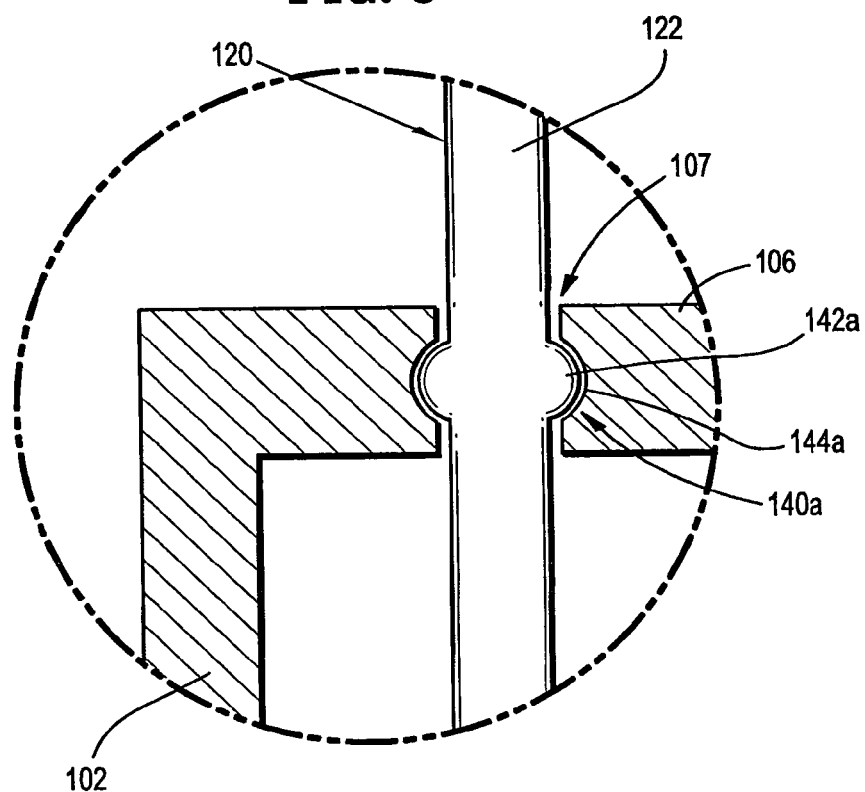
FIG. 4 is an enlarged side view of the area indicated as 4 of FIG. 2.
Figure 15:
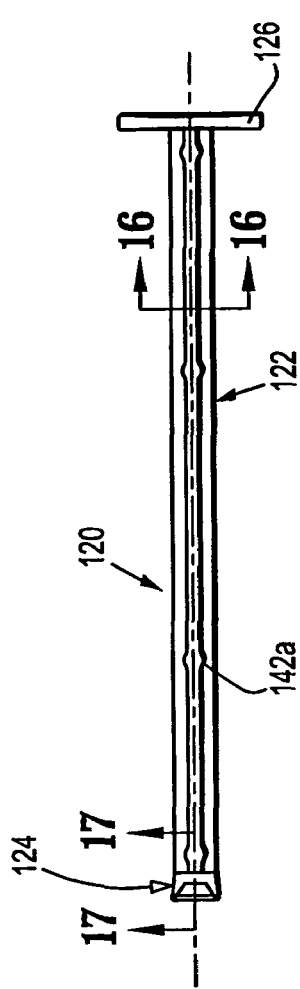
FIG. 15 is a top plan view of the plunger assembly of FIG. 14.
Figure 14:
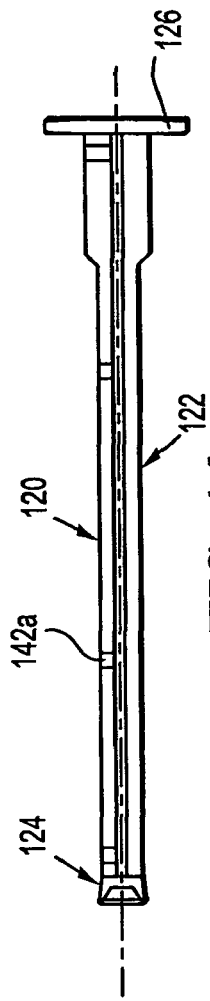
FIG. 14 is a side elevational view of the plunger assembly of the sampling device of FIGS. 1 to 4.
Figure 17:
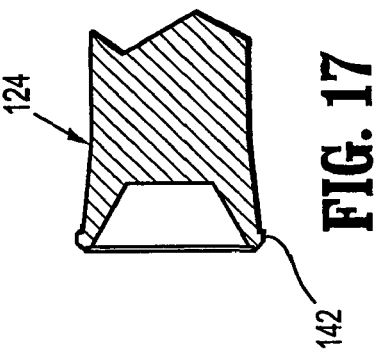
FIG. 17 is a cross-sectional view of the plunger assembly of FIGS. 14 and 15, as taken through 17-17 of FIG. 15.
Figure 16:
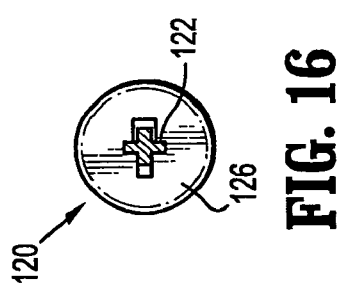
FIG. 16 is a cross-sectional view of the plunger assembly of FIGS. 14 and 15, as taken through 16-16 of FIG. 15.
Figure 18:
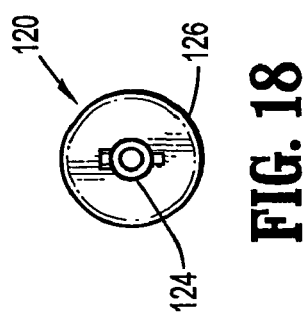
FIG. 18 is a front end view of the plunger assembly of FIG. 14.

As seen in FIG. 4, sampling device 100 can include feedback elements 140a including a series of nubs or projections 142a, preferably an annular nub or projection, extending radially outward from the surface of and along the length of piston rod 122 of plunger assembly 120 and an annular groove 144a formed along the inner periphery of opening 107 of proximal end 106 of body portion 102. Projections 142a are preferably spaced a fixed distance from one another, e.g., a distance equal to the equivalent of about 100 μL and/or about 150 μL of material in chamber 104 of body portion 102. Preferably, projections 142a and annular groove 144a have complementary cross-sectional profiles (e.g., rounded, pointed, squared and the like). In this manner, as plunger assembly 120 is displaced through body portion 102, projections 142a engage and disengage groove 144a. The engagement and disengagement of projections 142a with groove 144a creates at least one of an audile sound (e.g., a click) and/or a vibration or other tactile effect due to the temporary interruption of the smooth passage of piston rod 122 through opening 107 of proximal end 106 of body portion 102.

While feedback elements 140a include an annular projections 142a extending from piston rod 122 and an annular groove 144a formed in the periphery of opening 107 of proximal end 106 of body portion 102, it is envisioned that feedback elements 140a can include annular grooves formed in the outer surface of piston rod 122 and a projection, preferably an annular projection, extending radially inward from the periphery of opening 107 of proximal end 106 of body portion 102 (not shown).

Turning now to FIGS. 5A to 5E, a method of collecting a sample of material with sampling device 100 will be shown and described. As seen in FIG. 5A, distal end 102 of sampling device 100 is placed in contact with material to be collected "M". Preferably, stopper 124 is positioned in close proximity to opening 109 of distal end 108 of body portion 102.

As seen in FIG. 5B, body portion 102 of sampling device 100 is driven into material "M", in the direction of arrow "A". In so doing, as body portion 102 is driven into material "M", material "M" enters chamber 104 through opening 109 of distal end 108 and thereby displaces plunger assembly 120 in a direction opposite the direction of body portion 102, i.e., opposite to direction "A".

As seen in FIG. 5C, body portion 102 is driven into material "M" until the desired and/or necessary quantity of material "M" is "drawn" into chamber 104 of body portion 102. As more material "M" is "drawn" into chamber 104, driving plunger assembly 120 in a direction opposite to the relative direction of movement of body portion 102, feedback elements 140, 140a provide the user with an indication as to the quantity of material "M" contained in chamber 104. For example, one "click" would indicate that approximately 100 μL L and/or 150 μL of material "M" was "drawn" into chamber 104, and that each "click" would indicate that an additional 100 μL and/or 150 μL was "drawn" into chamber 104.

As seen in FIG. 5D, with the desired amount of material "M" within chamber 104, sampling device 100, at least body portion 102, is rotated, as indicated by arrow "B", an amount sufficient for cutting element 130 to free the sample of material "S" contained in chamber 104 from the remainder of material "M". With sample "S" free from material "M", sampling device 100 is withdrawn from material "M" while maintaining the position of plunger assembly 120 relative to body portion 102.

Turning now to FIG. 6, a method of expelling sample "S" from sampling device 100 will be shown and described. In order to expel, sample "S" from chamber 104 of body portion 102, plunger assembly 120 is displaced in a distal direction, e.g., in the direction of arrow "A", relative to body portion 102. As plunger assembly 120 is driven in a distal direction, stopper 124 forces sample "S" out opening 109 of distal end 108 of body portion 102. In use, feedback elements 140 or 140a, as described above, provide the user with audible and/or tactile indication and/or feedback as to the position of plunger assembly 120 relative to body portion 102 and, more particularly, the quantity of sample "S" expelled from chamber 104 of body portion 102.

As described above, each inter-engagement of annular projection 142 with annular groove 144 represents approximately and, more preferably, exactly 300 μL of sample "S" being expelled from chamber 104 of body portion 102.

While chamber 104 preferably has a volume of at least about 300 μL, it is envisioned that chamber 104 can have any practical volume. In a preferred embodiment, chamber 104 has a volume from at least about 600 μL to about 1000 μL. In addition, while inter-engagement of projection 142 with annular grooves 144 is described as occurring at each 100 μL, 150 μL, 200 μL or 300 μL increments, it is envisioned that such inter-engagement can occur at any volumetric increment.

It will be understood that various modifications may be made to the embodiments disclosed herein. For example, plunger assembly 120 can be provided with a handle 126 secured to proximal end 122a of piston rod 122 for facilitating the displacement of plunger assembly 120 relative to body portion 102.

Figure 20:
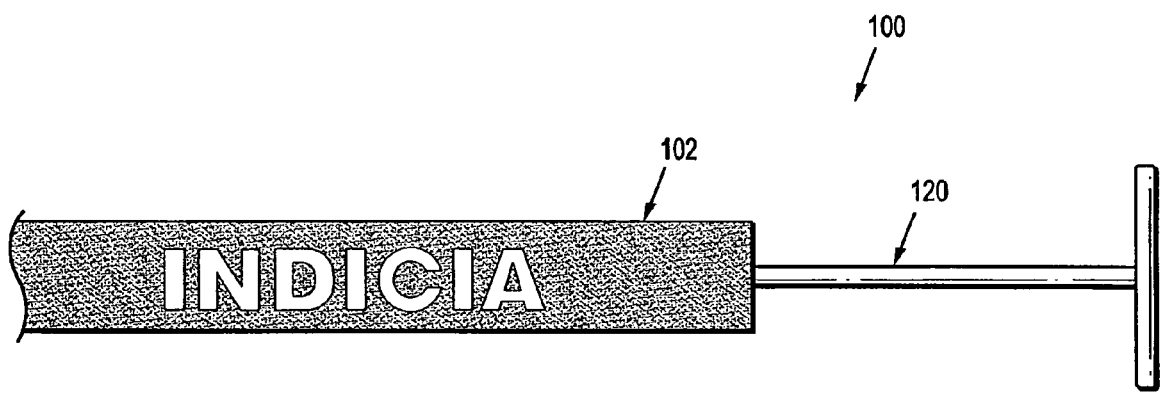
FIG. 20 is an enlarged side elevational view of the sampling device of FIG. 1 illustrating indicia formed on an outer surface thereof.

As seen in FIG. 20, it is envisioned that the outer and/or the inner surface of body portion 102 is frosted. Moreover, indicia (e.g., a company logo, etc.) may be provided on the outer surface of body portion 102 by not frosting the areas where the indicia is to appear or by frosting the areas where the indicia is to appear by a different degree as compared to the remainder of body portion 102.

Turning now to FIGS. 28-38, sampling devices 200, in accordance with alternate embodiments of the present disclosure will be shown and described. Sampling devices 200 are similar to sampling device 100 and will only be discussed in detail to the extent necessary to identify differences in construction and operation. In FIGS. 28-38, the elements of sampling device 200, corresponding elements from sampling device 100 of FIGS. 1-27, will be identified with corresponding reference characters.

Sampling device 200 includes a hollow cylindrical or tubular body portion 202 defining a chamber 204 therein. Body portion 202 includes a proximal end 206 having an opening 207 and a distal end 208 having an opening 209. Distal end 208 is adapted to form a slicing edge 210. Body portion 202 is further provided with metrical markings 212 for use in determining the volume of material within chamber 204 and, in turn, the volume of material to be expunged from chamber 204.

Sampling device 200 further includes a plunger assembly 220 slidably positionable within chamber 204 of body portion 202. Plunger assembly 220 includes a piston rod 222 including a proximal end portion 222a extending from proximal end 206 of body portion 202 and a distal end portion 222b extending into chamber 204 of body portion 202. Plunger assembly 220 further includes a stopper 224 operatively connected to distal end portion 222b of piston rod 222.

Preferably, as best seen in FIGS. 28, 30, 31 and 38, piston rod 222 has a generally cruciform transverse cross-sectional profile defining four (4) longitudinally extending walls 226a. While four (4) walls are shown and described, it is envisioned and within the scope of the present disclosure that any number of walls 226a may be provided, including and not limited to three, five, six, etc, or that rod 222 may be circular, rectangular or other cross-sectional shapes. Each wall 226a is provided with a series of projections 226b formed along an outer edge thereof. Each projection 226b includes a dimple or depression 226c formed in an apex thereof. Preferably, walls 226a and projections 226b are sized such that projections 226b are in close proximity with an inner surface of body portion 202. The projections 226b and dimples 226c form a part of a feedback element 244.

As best seen in FIG. 30, an annular race, recess or ring 250 is preferably formed in the inner surface of and at or near slicing edge 210 of body portion 202. Annular race 250 is dimensioned to receive annular projection 242 extending around stopper 224. Annular projection 242 is substantially similar to projection 142 of stopper 124 (see FIG. 17). Annular recess 250 allows for the distal end of stopper 242 to be in a less compressed position during shipping and storage.

As best seen in FIG. 31, feedback element 244 further includes an annular rib 243 formed along the inner surface of chamber 204 of body portion 202. Preferably, annular rib 243 is formed at, near, or some distance in from (distally of) opening 207 of proximal end 206 of body portion 202. According, as plunger assembly 220 is axially displaced relative to body portion 202, dimples 226c of projections 226b of piston rod 222 inter-engage with annular rib 243 of body portion 202 to provide the user with tactile and/or audible feedback. Preferably, dimples 226c and projection 226b are formed at locations along piston rod 222 corresponding to 150 μL of volume of chamber 204 of body portion 202.

As seen in FIGS. 29 and 30, a cutting element 230a may be provided at distal end 208 of body portion 202. Cutting element 230a extends across distal end 208 of body portion 202. Preferably, as best seen in FIG. 30, cutting element 230a is arcuate and extends proximally into body portion 202. Alternatively, as described above, cutting element 230a can extend directly across (diametrically across) body portion 202.

Figure 33:
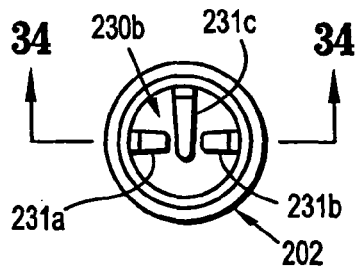
FIG. 33 is a distal end view of the sampling device of FIG. 32.
Figure 32:
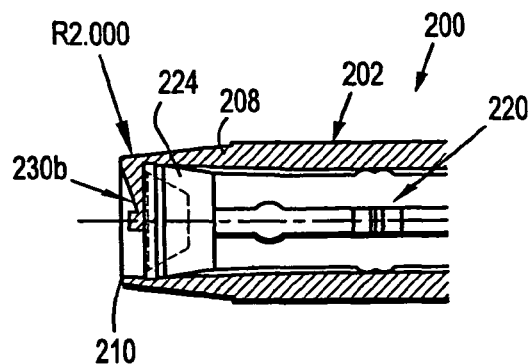
FIG. 32 is a longitudinal cross-sectional view of a distal end of a sampling device in accordance with still another embodiment of the present disclosure.
Figure 34:
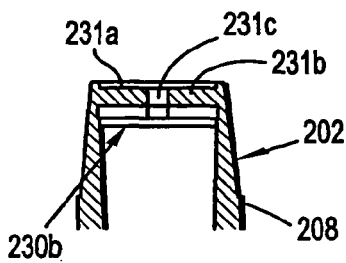
FIG. 34 is a cross-sectional view of the distal end of the sampling device of FIGS. 32 and 33, as taken through 34-34 of FIG. 33.

Turning now to FIGS. 32-34, a cutting element 230b, in accordance with another embodiment of the present disclosure, may be provided at distal end 208 of body portion 202. Cutting element 230b includes a pair of arms/fingers 231a, 231b extending radially inward and angled into body portion 202. Preferably, arms 231a, 231b terminate at a distance spaced from a central longitudinal axis of body portion 202. Cutting element 230b further includes a third arm/finger 231c extending radially inward from body portion 202 in a manner such that a distal end of third arm 231c extends between the pair of opposed arms 231a, 231b and beyond the central longitudinal axis of body portion 202. While cutting element 230b has been shown with three arms 231a-231c, it is envisioned and within the scope of the present disclosure that cutting element 230b may be provided with only third arm 231c extending radially inward from body portion 202 and terminating at a location beyond the central longitudinal axis of body portion 202.

Figure 36:
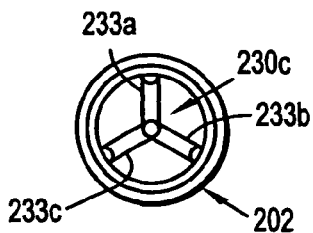
FIG. 36 is a distal end view of the sampling device of FIG. 35.
Figure 35:
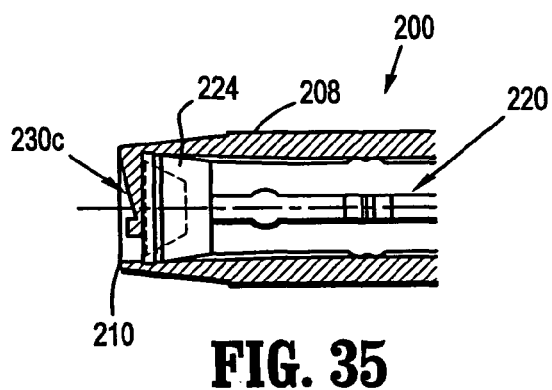
FIG. 35 is a longitudinal cross-sectional view of a distal end of a sampling device in accordance with another embodiment of the present disclosure.

Turning now to FIGS. 35 and 36, a cutting element 230c, in accordance with another embodiment of the present disclosure, may be provided at distal end 208 of body portion 202. Cutting element 230c includes a plurality of radially converging arms/fingers 233a-233c extending radially inward and at an angle into body portion 202 in such a manner that the distal ends of arms 233a-233c are joined to one another. Preferably, arms 233a-233c are joined at a location axially aligned with the central longitudinal axis of body portion 202. While three arms 233a-233c are shown it is envisioned and within the scope of the present disclosure, that any number of arms may be provided. Preferably, arms 233a-233c are spaced an equal radial distance from one another (e.g., 120°), however, it is envisioned and within the scope of the present disclosure that arms 233a-233c may be spaced any radial distance from one another.

In operation, as body portion 202 is rotated about its longitudinal axis, following insertion into the material "M" to be sampled, cutting elements 230a, 230b and 230c completely separate the sample "S", contained in chamber 204 of body portion 202, from the remainder of material "M".

Figure 37:
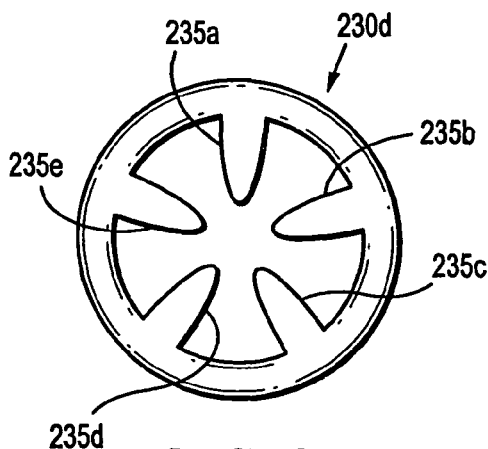
FIG. 37 is a distal end view of a sampling device illustrating a cutting element according to an alternate embodiment of the present disclosure.
Figure 38:
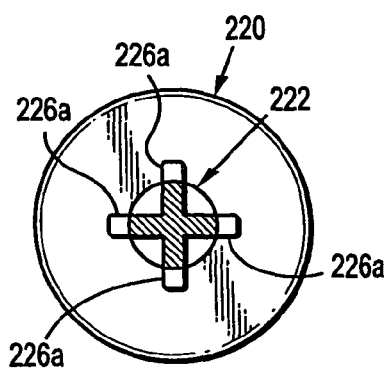
FIG. 38 is a transverse cross-sectional view of the sampling device of FIGS. 28-31 as taken through 38-38 of FIG. 28.

In an alternate embodiment, as seen in FIG. 37, cutting element 230d may be provided with a plurality of radially inward converging arms/fingers 235a-235e extending from body portion 202. In this embodiment, the distal ends of arms 235a-235e do not contact and/or are not joined with one another, and none of the distal ends of arms 235a-235e extend across the central longitudinal axis of body portion 202. In this manner, in operation, when body portion 202 is rotated within material "M", about its longitudinal axis, the portion of sample "S" of material "M", located along the central longitudinal axis of body portion 202, is not directly separated from the remainder of material "M" by arms 235s-235e.

Figure 39:
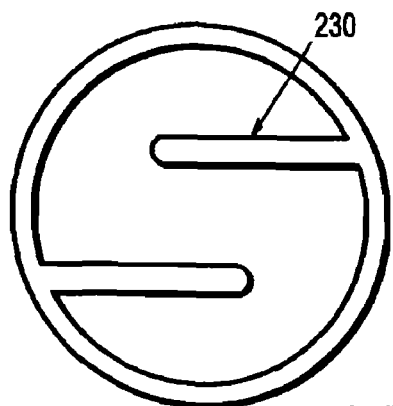
FIG. 39 is a distal end view of a sampling device illustrating a cutting element according to another alternate embodiment of the present disclosure.
Figure 40:
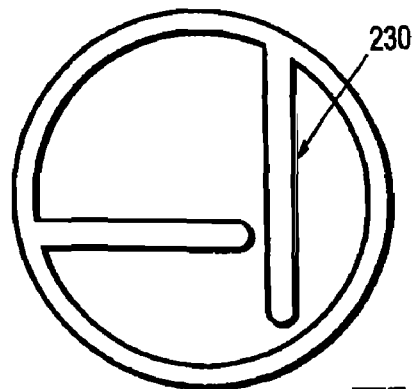
FIG. 40 is a distal end view of a sampling device illustrating a cutting element according to still another alternate embodiment of the present disclosure.
Figure 41:
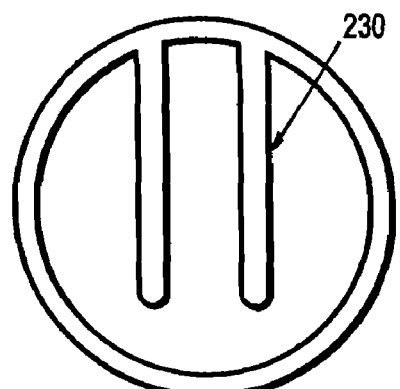
FIG. 41 is a distal end view of a sampling device illustrating a cutting element according to yet another alternate embodiment of the present disclosure.

As seen in FIGS. 39-41, other possibilities for cutting element 230 exist. For example, cutting element 230 may include a pair of laterally spaced apart parallel arms extending inward from substantially opposite sides of body portion 202 (FIG. 39); a pair of arms extending inward from body portion 202 and at an angle, preferably orthogonal, to one another (FIG. 40); and a pair of laterally spaced apart parallel arms extending inward from substantially a common side of body portion 202 (FIG. 41). Preferably, each arm of cutting elements 230 shown in FIGS. 39-41 include a free end which is not connected to body portion 202. However, it is envisioned that the free end of each or any number of the arms may be secured to body portion 202.

Accordingly, the above description should not be construed as limiting, but merely as an exemplification of preferred embodiments. Those skilled in the art will envision other modifications within the scope and spirit of the claims appended hereto.

What is claimed is:

1. A method of collecting a sample of material from a body, comprising the steps of:
  providing a device for obtaining the sample of material, the device comprising:
    a tubular body portion having an open distal end and defining a chamber for receiving the sample of material therein;
    a plunger assembly operatively associated with the tubular body portion and having a stopper slidably disposed within the chamber of the body portion, the stopper being adapted for fluid tight engagement with the body portion;
    feedback elements provided on at least one of the tubular body portion and the plunger assembly for providing a user of the sampling device with at least one of audible and tactile indications regarding an amount of displacement of the plunger assembly relative to the body portion; and
    a plurality of cutting elements extending radially inwardly from the open distal end of the tubular body portion and angled into the tubular body portion, each of the cutting elements having an unsupported free end disposed within the tubular body portion, wherein the cutting element includes: a pair of opposed arms extending toward the longitudinal central axis of the body portion; and a third arm extending beyond the longitudinal central axis of the body portion, the third arm being disposed at a substantially equi-distant location between the pair of opposed arms;

placing the open distal end of the device against the material from which the sample is to be taken;

driving the body portion into the material an amount sufficient for a sample of the material to enter the chamber of the body portion;

rotating the body portion about a longitudinal axis thereof an amount sufficient for the cutting element to sever the sample of material from the remainder of the material; and withdrawing the device from the remainder of the material.

2. The method according to claim 1, wherein the stopper of the plunger assembly is positioned proximate the distal end of the body portion when the device is driven into the material.

3. The method according to claim 2, wherein as the body portion is driven into the material the stopper is displaced in an axially proximal direction relative to the body portion.

4. The method according to claim 1, wherein the feedback elements include:

a series of annular grooves formed along the length of the chamber; and a projection extending radially outward from the stopper of the plunger assembly.

5. The method according to claim 4, wherein as the stopper is displaced in an axially proximal direction relative to the body portion, the projection of the stopper inter-engages with the annular grooves formed in the chamber.

6. The method according to claim 4, wherein the annular grooves are provided at intervals which correspond to 150 µL of volume of the chamber of the body portion.

7. The method according to claim 4, wherein the body portion includes a metrical marking for each annular groove.

8. The method according to claim 1, wherein, as the body portion is driven into the material, the feedback elements provide the user with at least one of audible and tactile indications as to the volume of material collected into the chamber of the body portion.

9. The method according to claim 1, further comprising the step of driving the plunger assembly in a distal direction relative to the body portion to expel the sample therefrom.

10. The method according to claim 9, wherein the feedback elements provide the user with at least one of audible and tactile indications as to the quantity of sample expelled from the chamber of the body portion.

11. A device for obtaining a sample from inside a body, comprising:

a tubular body portion defining a chamber for receiving a sample of material therein, the body portion having an open distal end, a proximal end and defining a longitudinal central axis;

a plunger assembly operatively associated with the tubular body portion, the plunger assembly having a stopper slidably disposed within the chamber of the body portion, the stopper being adapted for fluid tight engagement with the body portion;

feedback elements provided on at least one of the tubular body portion and the plunger assembly for providing a user of the sampling device with at least one of audible and tactile indications regarding an amount of displacement of the plunger assembly relative to the body portion; and a cutting element having a plurality of arms extending radially inwardly from the open distal end of the tubular body portion and angled into the tubular body portion, each of the arms having an unsupported free end disposed within the tubular body portion, wherein the cutting element includes:

a pair of opposed arms extending toward the longitudinal central axis of the body portion; and a third arm extending beyond the longitudinal central axis of the body portion, the third arm being disposed at a substantially equi-distant location between the pair of opposed arms.

12. The device according to claim 11, wherein the feedback elements include one of a groove and a projection formed along an inner surface of the chamber of the tubular body portion.

13. The device according to claim 12, wherein the groove and projection are annular.

14. The device according to claim 13, wherein the annular groove corresponds with a metrical marking provided on the tubular body portion.

15. The device according to claim 11, wherein the tubular body portion includes a series of metrical markings formed along the length thereof, and wherein a feedback element is provided in association with each metrical marking.

16. The device according to claim 11, wherein the open distal end of the tubular body portion has a frusto-conical shape over at least one of its outer and inner peripheries.

17. The device according to claim 11, wherein the tubular body portion defines a distal cutting edge.

18. The device according to claim 11, wherein the plunger assembly includes a rod operatively connected to the stopper and extending from the proximal end of the body portion.

19. The device according to claim 18, wherein the feedback elements include at least one of a series of grooves and a series of projections formed along the length of the rod.

20. The device according to claim 18, wherein the feedback elements include one of a groove and a projection provided at the proximal end of the tubular body for inter-engaging the grooves or projections formed on the rod.

21. The device according to claim 11, wherein at least one of the plurality of arms extends into the chamber of the body portion proximal to the end of the body portion.

* * * * *